United States Patent
Umeda

(10) Patent No.: US 7,121,826 B2
(45) Date of Patent: Oct. 17, 2006

(54) METHOD OF MANUFACTURING AN ORTHODONTIC MODEL, AND AN ORTHODONTIC MODEL PRODUCED THEREBY

(76) Inventor: Minoru Umeda, Rua Pamplona No. 50, Sao Paulo -SP (BR)

( * ) Notice: Subject to any disclaimer, the term of this patent is extended or adjusted under 35 U.S.C. 154(b) by 194 days.

(21) Appl. No.: 10/888,821

(22) Filed: Jul. 9, 2004

(65) Prior Publication Data

US 2006/0008775 A1    Jan. 12, 2006

(51) Int. Cl.
*A61C 1/14* (2006.01)
*A61C 3/04* (2006.01)

(52) U.S. Cl. .................. 433/49; 433/60; 433/213; 434/263

(58) Field of Classification Search .......... 433/49, 433/53, 54, 60, 213; 434/263, 264
See application file for complete search history.

(56) References Cited

U.S. PATENT DOCUMENTS

| | | | | | |
|---|---|---|---|---|---|
| 2,138,254 A | * | 11/1938 | Mink | .......... | 433/56 |
| 2,619,725 A | * | 12/1952 | Roeser | .......... | 433/60 |
| 3,576,075 A | * | 4/1971 | Scott | .......... | 433/34 |
| 3,882,602 A | * | 5/1975 | Polanco | .......... | 433/49 |
| 4,608,016 A | * | 8/1986 | Zeiser | .......... | 433/74 |
| 5,098,290 A | * | 3/1992 | Honstein et al. | .......... | 433/74 |
| 5,417,750 A | * | 5/1995 | Cohen et al. | .......... | 106/35 |
| 5,947,725 A | * | 9/1999 | Squicciarini | .......... | 433/60 |
| 6,210,160 B1 | * | 4/2001 | Shima | .......... | 433/60 |
| 2002/0164556 A1 | * | 11/2002 | Huffman | .......... | 433/60 |

* cited by examiner

*Primary Examiner*—Ralph A. Lewis
*Assistant Examiner*—Casey Donahoe
(74) *Attorney, Agent, or Firm*—Michael J. Striker

(57) ABSTRACT

An orthodontic model has a single block body made of catalyzing acrylic resin with a pair of prism boxes inversely positioned and interconnected by a pair of posterior walls with a window, the prism boxes have covers of the same shape and are provided with perimetral depressions for fitting to the boxes and to reach a welding of edges of each dental arch or the model, and a method of its production is proposed.

2 Claims, 4 Drawing Sheets

METHOD OF MANUFACTURING AN ORTHODONTIC MODEL, AND AN ORTHODONTIC MODEL PRODUCED THEREBY

BACKGROUND OF THE INVENTION

The present invention relates to a method of manufacturing orthodontic models, as well as to orthodontic models produced by the inventive method.

Orthodontic models are currently made of plaster or hard resin. In the first case, the piece is fragile and appears to be unsatisfactory as a result of the plaster physical limitations. Continuous handling leads to early wearing of the model and the test or steady prosthesis fitting is impaired.

Another problem is that the plaster model, as a result of its fragility, is difficult to handle during orthodontics exposures, in addition to not causing an adequate technical effect, since the plaster is white and does not allow contrast between gums and teeth. Another disadvantage to be considered is that, if a portion of the model breaks, restoration is extremely argos, thus preventing total repair.

Models made of hard resin are more resistant and the material color contrast (teeth and gums) facilitates the orthodontic model study by the orthodontic professional. However, considering the drawbacks, the hard resin models are heavy, difficult to manufacture and impose high operating cost. For this reason, it is first necessary to mold an alginate matrix inside the patient mouth. When dried, this flexible matrix form receives the resin that is poured to fill it completely, reaching the maximum level. Once the resin is cured, the piece is removed from its mold and the finishing work is then started. This work is slow and expensive since all imperfections of the piece need to be removed. Depending on the case, dental arch models made of hard resin can weigh up to 400 g. This excessive mass renders the piece fragile, as it can easily break if dropped.

SUMMARY OF THE INVENTION

It is therefore an object of the present invention to provide a method of manufacturing orthodontic models, and the models manufactured by this method, with the aim to provide a simpler manufacture, thus allowing a significant reduction of cost, and further a safe positioning of prosthesis in orthodontic models, such as implants, molded dental arches, etc.

In keeping with these objects and with others which will become apparent hereinafter, one feature of the present invention resides, briefly stated, in a method of manufacturing orthodontic models which includes providing a pair of prism boxes inversely positioned and interconnected by a pair of posterior walls with a window; providing covers having perimetric depressions for fitting purposes; reaching through the covers the prism boxes for fixing edges of an orthodontic model positioned between the prism boxes; and forming a model in alginate matrix by pouring white resin into cavities and brushing pink acrylic resin on matrix walls until a desired thickness is reached and the model is obtained.

It Is also an object of the present invention to provide an orthodontic model which has a single block body made of catalyzing acrylic resin and having a pair of prism boxes inversely positioned and interconnected by a pair of posterior walls provided with a window; covers having perimetric depressions for fitting purposes, such that through said covers it is possible to reach said prism boxes for fixing edges of an orthodontic model positioned between said prism boxes, said model being formed in alginate matrix by pouring white resin into cavities and brushing pink acrylic resin on a matrix walls until a desired thickness is reached and the model is obtained.

When the method of manufacturing orthodontic models is performed in accordance with the present invention, and an orthodontic model is formed in accordance with the present invention, the reductions in weight and final cost of the piece are obtained, an effective positioning of both dental arches (models) among each other is assured, and their correct positioning in relation to the patient's skull is simulated.

The support in accordance with the present invention is shaped as a single block die, comprising an upper portion and a lower portion, made of a plastic material, having displaceable covers and being a hollow, light and highly cheap piece, if compared to those currently known. Molding is carried out using catalyzing resins, so that the models melt with the support molds, thus forming a single piece.

The manufacturing includes, first of all, in producing a conventional alginate matrix that is previously prepared to receive the resin. Unmolding agents are applied for that purpose. Next, the teeth are formed in the matrix by pouring white resin into the cavities. After that, pink acrylic resin is brushed on the matrix walls until the desired thickness is reached to obtain the dental arch.

Once molded the arch is removed from the alginate matrix. Its edges are cut, and it is then fit into the die having an upper and a lower portion. When fitted, the arch model is correctly positioned in the die, thus reassembling the lower and upper arches to each other. Next, the gaps are filled with non-adherent mass, the resin is placed and the models are then welded to the die. Next, the assembly undergoes a lapidary/burring work and the dental arches are finished using a varnish.

Since the arches are hollow, both sides of the die receives closing covers, thus finishing the piece.

It is critical to remember that the entire manufacturing processing of the arch and the resin cure is carried out in an oven at approximately 40° C. The final piece weight should not exceed approximately 30 g.

The proposed manufacturing system is completely feasible at a low cost. The new solution is practical if compared to the above mentioned old solutions having problems. Its characteristics offer highly satisfactory technical effects, such as simplicity, durability, robustness, low manufacturing cost, etc.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
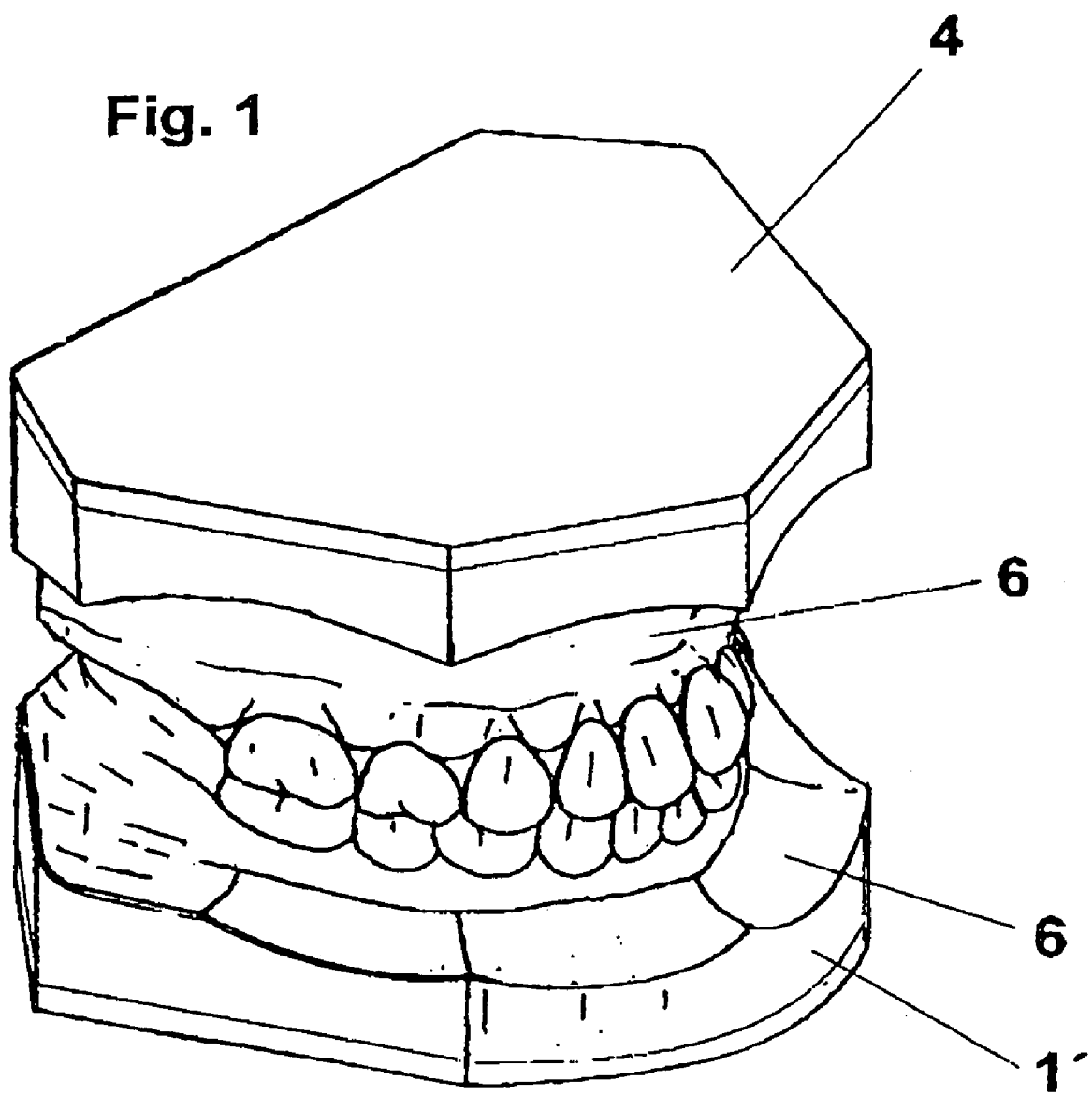
FIG. 1 is a perspective view of a support, having orthodontic models molded on it, in accordance with the present invention.
Figure 2:
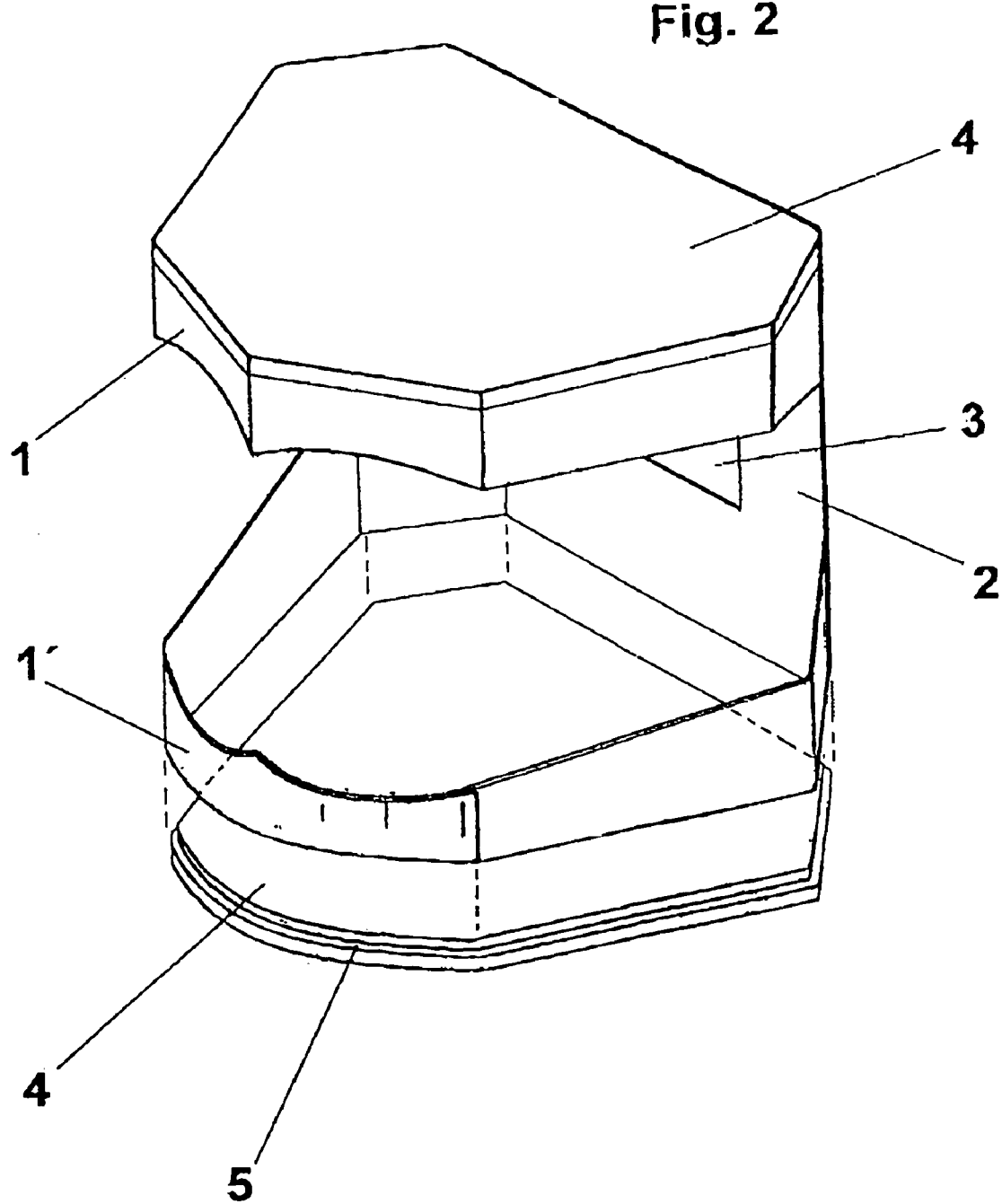
FIG. 2 is view showing the support for the orthodontic models, with a lower cover being removed.
Figure 3:
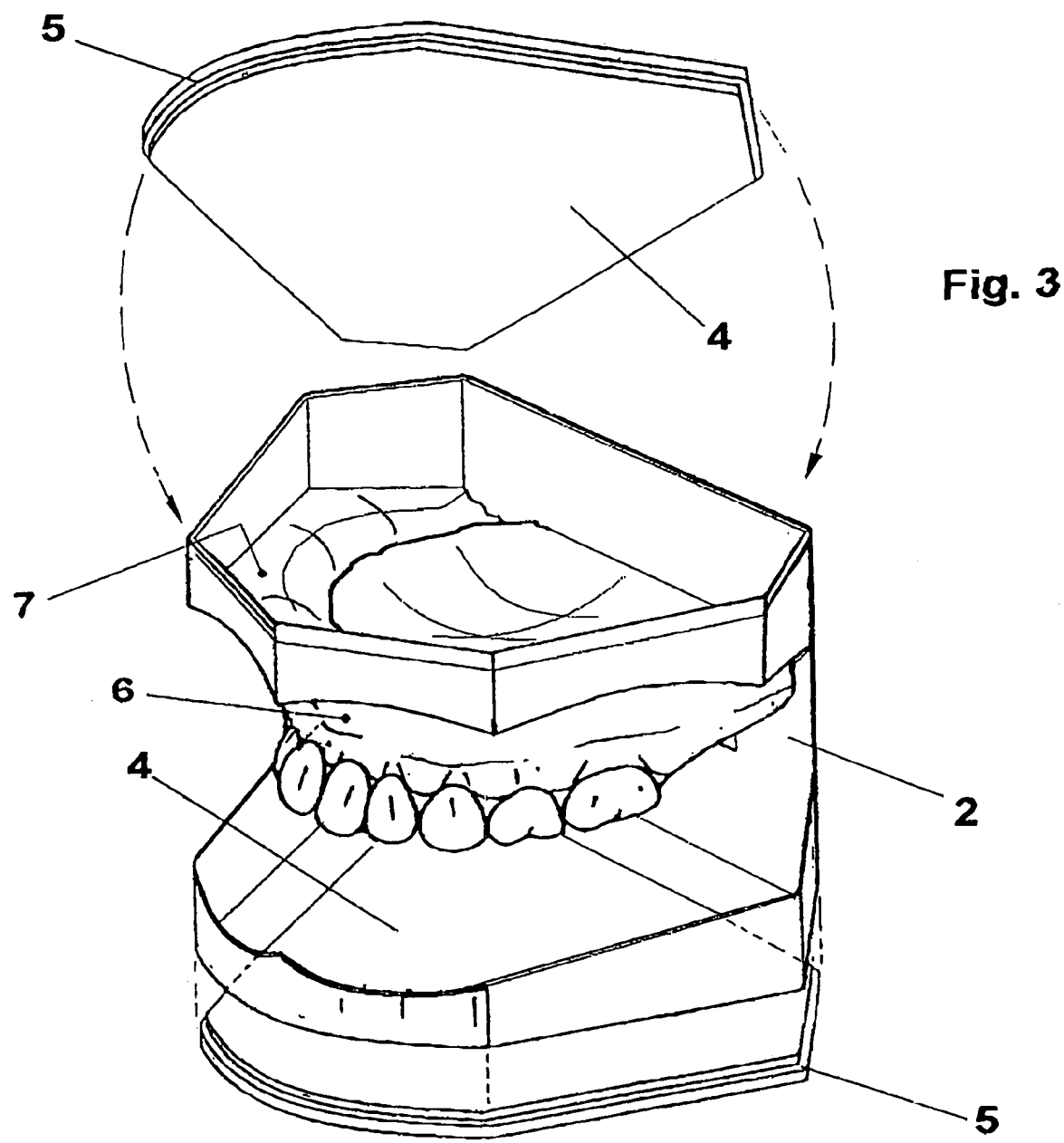
FIG. 3 is a view showing a support with an upper orthodontic model, both upper and lower covers being removed.
Figure 4:
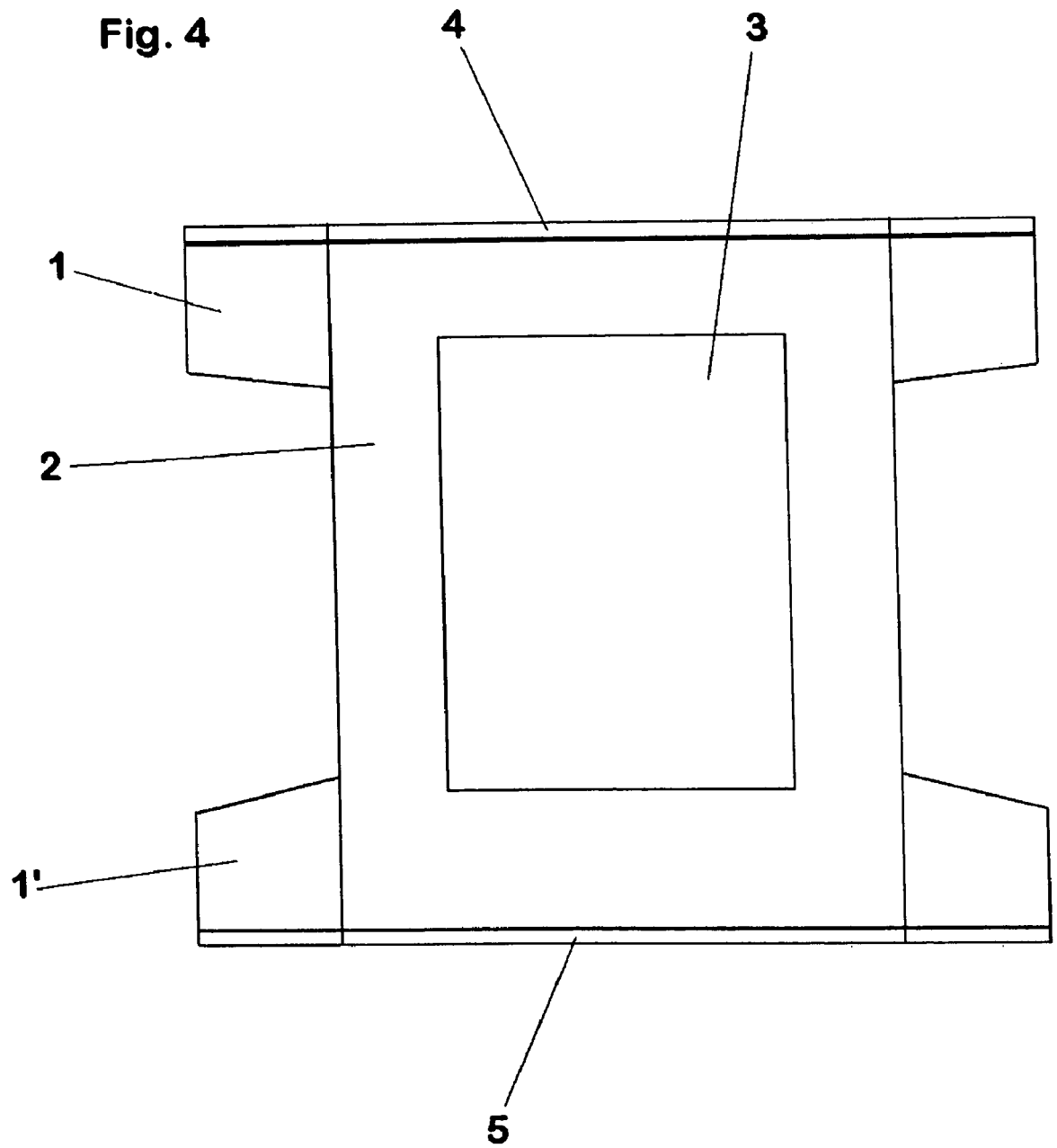
FIG. 4 is a view showing posterior walls of the support.

In accordance with the present invention, a single block body is made of catalyzing acrylic resin. The body is composed of a pair of prism boxes 1, 1' which are inversely positioned and interconnected by a pair of posterior walls 2, provided with a window 3.

Both prism boxes 1', 1' have covers 4. The covers have the same shape and are provided with perimetric depressions 5 for fitting purposes.

When the covers 4 are removed, it is possible to widely reach the inside of the single block body, that is through the prism boxes 1, 1' so that the orthodontic models 6 can be fixed, positioned between both prism boxes 1, 1'. Once fixed, the covers 4 are simply placed, and the assembly is ready for use.

The teeth are formed in the alginate matrix by pouring white resin into the cavities. After that, pink acrylic resin is brushed on the matrix walls until the desired thickness is reached to obtain the dental arch 6. Each arch 6 is fitted inside the die formed by the prims boxes 1, 1' and correctly positioned. The gaps are being filled with non-adherent mass. The resin is placed and the edges 7 are then welded to the die.

It will be understood that each of the elements described above, or two or more together, may also find a useful application in other types of constructions differing from the types described above.

While the invention has been illustrated and described as embodied in a method of manufacturing an orthodontic model, and an orthodontic model produced thereby, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A method of manufacturing an orthodontic model assembly, comprising the steps of:
   making a single block body composed of catalyzed acrylic resin and having a pair of prism boxes inversely positioned and interconnected by a pair of posterior walls with a window,
   wherein making a single block body composed of catalyzed acrylic resin includes forming orthodontic models in alginate matrix by pouring white acrylic resin into the matrix cavities and brushing pink acrylic resin on the matrix walls until a desired thickness is reached and the models are obtained;
   providing covers having perimetric depressions for fitting the covers to the prism boxes;
   and reaching through the prism boxes, when the covers are removed, for fixing the edges of the orthodontic models positioned between the prism boxes.

2. An orthodontic model assembly, comprising:
   a single block composed of catalyzed acrylic resin and having a pair of prism boxes inversely positioned and interconnected by a pair of posterior walls provided with a window,
   wherein the single block body composed of catalyzed acrylic resin comprises orthodontic models formed in alginate matrix by pouring white acrylic resin and brushing pink acrylic resin on the matrix walls until a desired thickness is reached and the orthodontic models are obtained;
   and covers having perimetric depressions for fitting the covers to said prism boxes, such that when said covers are removed it is possible to reach through said prism boxes for fixing the edges of the orthodontic models positioned between said prism boxes.

* * * * *